(12) United States Patent
Danger

(10) Patent No.: US 7,887,326 B2
(45) Date of Patent: Feb. 15, 2011

(54) INSTRUMENT SHAFT FOR A ROTATING INSTRUMENT

(75) Inventor: Karl-Heinz Danger, Detmold (DE)

(73) Assignee: Gebr. Brasseler GmbH & Co. KG (DE)

(*) Notice: Subject to any disclaimer, the term of this patent is extended or adjusted under 35 U.S.C. 154(b) by 101 days.

(21) Appl. No.: 11/998,598

(22) Filed: Nov. 30, 2007

(65) Prior Publication Data
US 2008/0138762 A1 Jun. 12, 2008

(30) Foreign Application Priority Data
Dec. 5, 2006 (DE) .................. 20 2006 018 407 U

(51) Int. Cl.
A61C 3/02 (2006.01)
(52) U.S. Cl. ...................... 433/165; 408/226
(58) Field of Classification Search .................. 433/50, 433/127, 128, 146, 147, 165, 166; 606/79, 606/80, 81; 406/226; 408/226
See application file for complete search history.

(56) References Cited

U.S. PATENT DOCUMENTS 477,225 A * 6/1892 Rauhe .................. 433/165
6,607,533 B2 * 8/2003 Del Rio et al. ............. 606/80
2002/0028422 A1 3/2002 Kumar
2006/0127847 A1 * 6/2006 Danger et al. ............. 433/165

FOREIGN PATENT DOCUMENTS

| DE | 28 34 156 C3 | 7/1981 |
| DE | 196 15 101 A1 | 10/1997 |
| DE | 203 14 717 U1 | 2/2004 |
| DE | 10 2005 050 329 B3 | 5/2007 |
| GB | 2 123 523 A | 2/1984 |
| JP | 2002-257148 | 9/2002 |

OTHER PUBLICATIONS

Search Report from correspondingGerman Patent Application No. DE 20 2006 018 407.4, dated Sep. 24, 2007.
Search Report from correspondingEPO Patent Application No. EP 07022975.2, dated Mar. 14, 2008.

* cited by examiner

Primary Examiner—Cris L Rodriguez
Assistant Examiner—Eric Rosen
(74) Attorney, Agent, or Firm—Bliss McGlynn, P.C.

(57) ABSTRACT

A dental instrument shaft for a rotating instrument made of a ceramic material includes a cylindrical shaft end having a center axis and a flat driving area arranged in parallel to the center axis, wherein a groove having a cross-section shaped as a pitch circle is formed at a transition region of the driving area to the cylindrical shaft end.

10 Claims, 3 Drawing Sheets

INSTRUMENT SHAFT FOR A ROTATING INSTRUMENT

BACKGROUND OF THE INVENTION

1. Field of the Invention

The present invention relates to an instrument shaft for a rotating instrument, the shaft being made of a ceramic material.

2. Description of the Related Art

Rotating instruments, in particular dental instruments, are generally made of metallic materials. The shaft which is inserted into a driving unit, e.g. an elbow fitting, has to be axially fixed for this purpose and also must be held suitably for inducing a torque. The dimensions of the instrument shafts result from ISO 1797. For the manufacture of instrument shafts made of specific ceramics, there result particular requirements with respect to the material characteristics. In this context, it has to be considered in particular that sharp edges having a notching effect may lead to failure cracks.

SUMMARY OF THE INVENTION

It is an object of the present invention to provide an instrument shaft made of a ceramic material, the shaft being compatible with ISO 1797 and featuring good material characteristics in combination with a long service life.

According to the present invention, this object is solved by the combination of features of claim 1, the sub-claims disclose further advantageous embodiments of the invention. According to the present invention, it is thus provided that a groove is formed at the transition region of the driving area to the cylindrical shaft end, the groove having a cross-section in the shape of a pitch circle.

The inventive instrument shaft features a high extent of mechanic stability and a small to no susceptibility to cracks, since tension peaks in the transition area from the cylindrical shaft to the flattened plane driving area are prevented by the groove.

Consequently, an increase of the torsion moment by at least 20% is possible according to the present invention. This results in an increased operating safety as well as prolongation of the service life of the instruments.

According to the present invention, it is therewith provided that the groove is arranged in the transition area between the flat driving area and a substantially flat end of the cylindrical portion of the shaft end extending in a radial direction.

In one embodiment of the present invention, the groove is formed straight and extends transverse across the complete width of the driving area.

Concerning the position of the groove, in particular with respect to the position of the center axis of the groove, different variations are provided according to the present invention, which may be selected in accordance with the dimension of the shaft end and/or the material.

According to the present invention, it is therefore possible to position the center axis of the groove such that the groove is arranged radially in the end portion of the driving area and therewith does not extend into the radial edge or surface of the cylindrical part of the shaft end. Correspondingly, it is also possible, according to the present invention, not to indent the groove into the driving area, but to insert same exclusively into the end edge or end surface of the cylindrical shaft portion.

According to the present invention, it is further possible to insert the groove transversely such that it extends into the driving area as well as into the radial portion of the shaft end. Furthermore, it is also possible, according to the present invention, to provide the groove with an outlet bevel which is arranged either toward the driving area or toward the radial surface of the shaft end.

In a further embodiment of the present invention, it is also possible to form the groove as an annular groove which extends from the lateral portions of the driving area.

The tension load occurring during the operation of the instrument may be considerably enhanced by the following aspects according to the invention:

An ideal relationship between the cut-in depth of the groove and the shaft diameter of the shaft end lies in a range of 0.05/2.35 to 0.5/2.35. A particularly preferred range lies between 0.05/2.35 and 0.2/2.35. The values are respectively given in mm, wherein a shaft diameter of 2.35 mm is underlying this example. Upon a modification of the shaft diameter, there result accordingly adjusted values.

According to the present invention, it is also particularly preferred that the relationship between cut-in width (width of the groove) and length of the driving area ranges between 0.1/2.6 and 0.8/2.6. In this context, it is particularly preferred if the range lies between 0.2/2.6 and 0.4/2.6. Also here, the values are given in mm. The relationship has to be modified accordingly in case of larger or smaller shafts. The radius of the groove is preferably between 0.15 and 0.2 mm according to the present invention.

From the above values and relationships, there result optimized conditions for the force transmission and the tension distribution. The present invention may be applied to all instruments made of high performance ceramics (also referred to as technical ceramics or engineer ceramics). This category includes single-substance or multi-substance oxide ceramics, which may be present as mixed oxide ceramics as well as dispersion ceramics. Examples include aluminum oxide ceramics, zirconium oxide ceramics, magnesium oxide or titanium oxide.

It is particularly preferred if, according to the present invention, the portion of the instrument shaft that is particularly loaded by tension, i.e. especially the portion of the groove is provided with a texture being densified by shot peening. This leads to a densification of the surface, which results in an increased strength. Corundum or aluminum oxide may, for example, be used for the shot peening.

Other objects, features, and advantages of the present invention will be readily appreciated, as the same becomes better understood, after reading the subsequent description taken in conjunction with the accompanying drawings.

DESCRIPTION OF THE PREFERRED EMBODIMENT(S)

Figure 1:
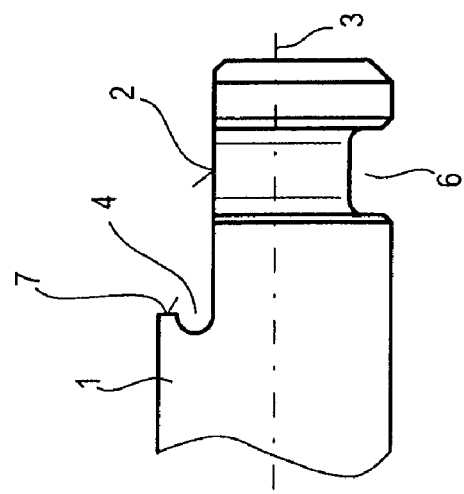
FIGS. 1 through 6 are lateral views of different embodiments of an inventive shaft end of an instrument shaft, according to the present invention.

Referring now to the drawings, and in particular FIG. 1, one embodiment of an instrument shaft, according to the present invention, is shown. In FIG. 1 to 6, identical parts are referred to with the same reference numerals. According to the present invention, the instrument shaft is cylindrical and comprises a cylindrical shaft end 1 having a center axis 3. A driving area 2 is formed at the shaft end 1, the driving area extending in parallel to the center axis 3 and having dimensions pursuant to ISO 1797.

Furthermore, the shaft end 1 comprises an axial groove 6 for axially securing the instrument shaft, which is also formed pursuant to ISO 1797.

According to the present invention, as shown in FIGS. 1 to 5, a groove 4 is provided which is formed straight and the center axis of which therewith extends in parallel to the driving area 2. The groove 4 is arranged at a transition region of the driving area 2 to a radial portion or a radial surface 7 of the shaft end 1.

FIG. 1 shows an embodiment in which the groove 4 is indented into the driving area 2, whereas the radial surface 7 lies adjacent to the border region of the groove 4 having the shape of a pitch circle.

Figure 2:
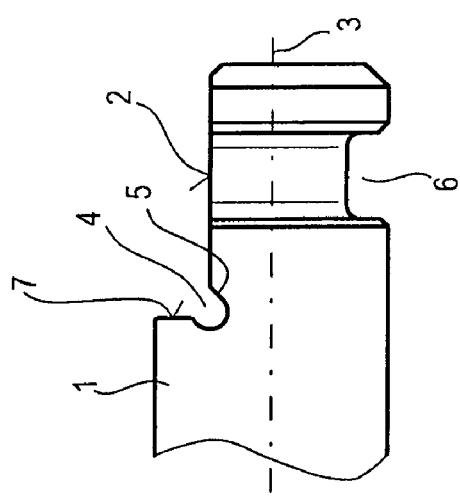

In the embodiment of FIG. 2, the groove 4 is arranged such that it is inserted into the driving area 2 as well as into the radial surface 7.

Figure 3:
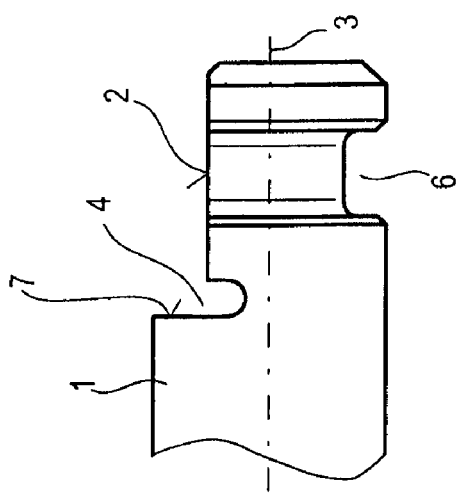

In the embodiment of FIG. 3, the groove 4 extends exclusively into the radial surface 7 such that the edge of the groove 4 shaped as a pitch circle or a half circle directly merges into the driving area 2.

Figure 4:
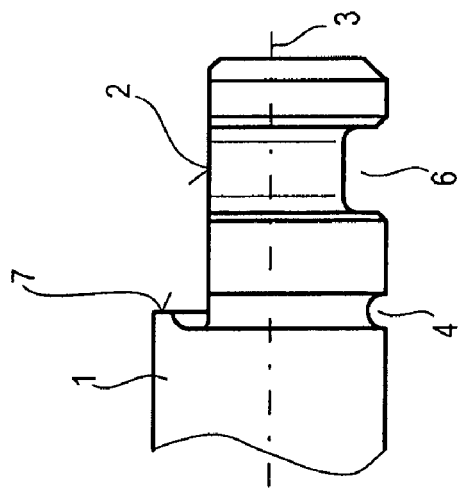
Figure 5:
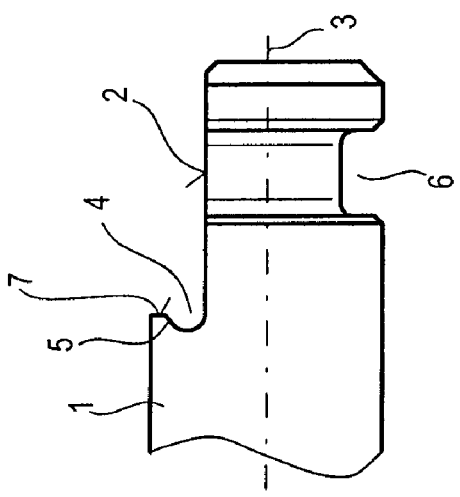

In the embodiments of FIGS. 4 and 5, an outlet bevel 5 is additionally provided, which either merges into the driving area 2 (FIG. 4) or into the radial surface 7 (FIG. 5).

Figure 6:
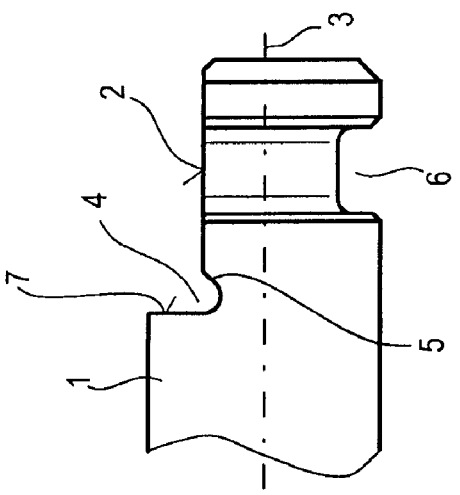

The embodiment of FIG. 6 shows a further inventive variation in which the groove 4 is formed as an annular groove extending from the lateral transition region of the driving area 2 around the shaft end 1.

Figure 7:
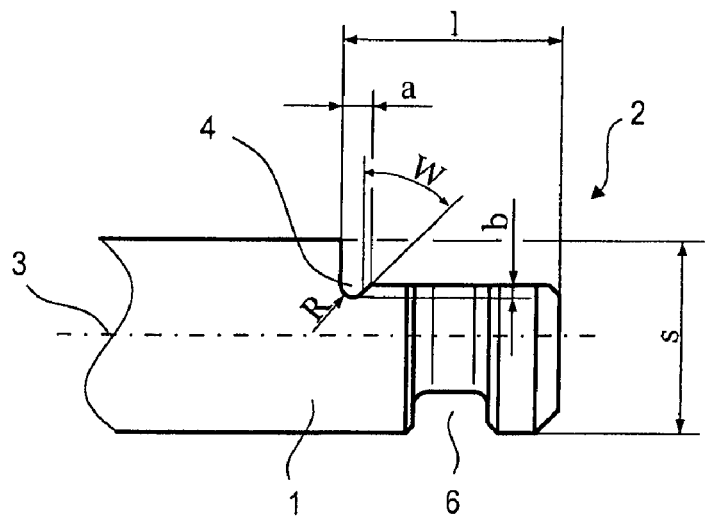
FIG. 7 is a view, analogous to FIGS. 1 to 6, from which the dimensions can be derived.

FIG. 7 shows a dimensioned illustration of the inventive instrument shaft, in which:

l is the length of the driving area 2;
s is the shaft diameter of the shaft end 1;
a is the cut-in width of the groove 4;
b is the cut-in depth of the groove 4;
W is the angle of the outlet bevel 5; and
R is the radius of the groove 4.

Figure 8:
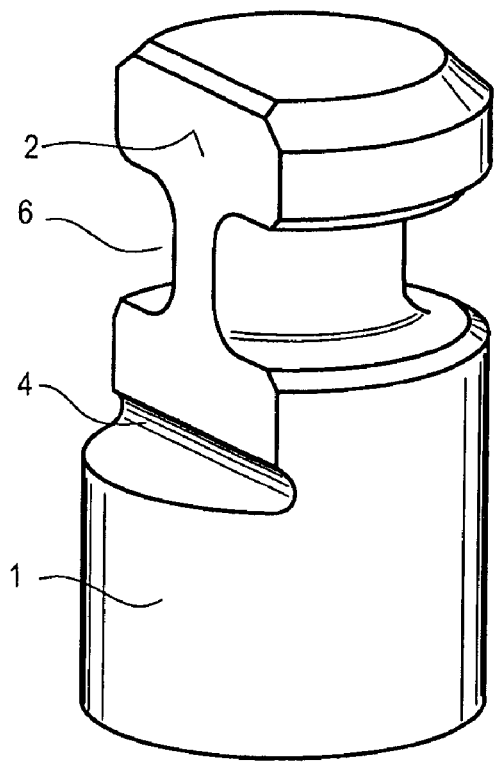
FIGS. 8 and 9 are perspective views, analogous to the embodiments of FIGS. 1 to 6.
Figure 9:
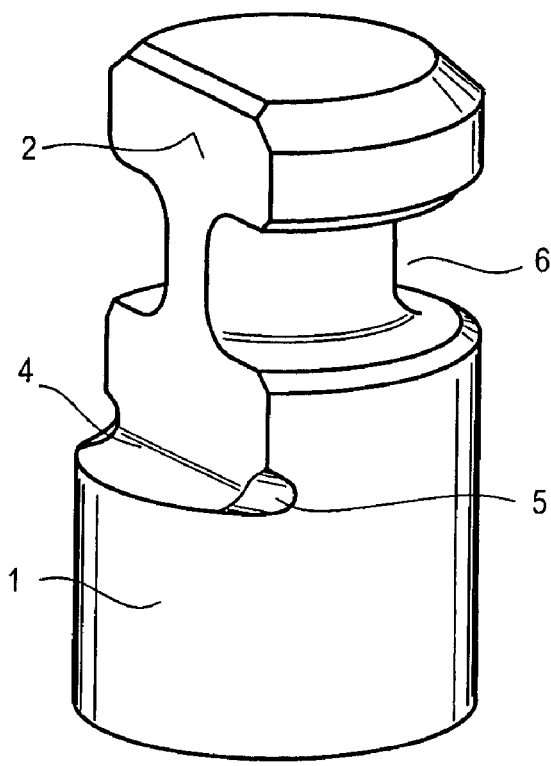

FIGS. 8 and 9 show perspective illustrations analogous to FIGS. 1 to 6.

Figure 10:
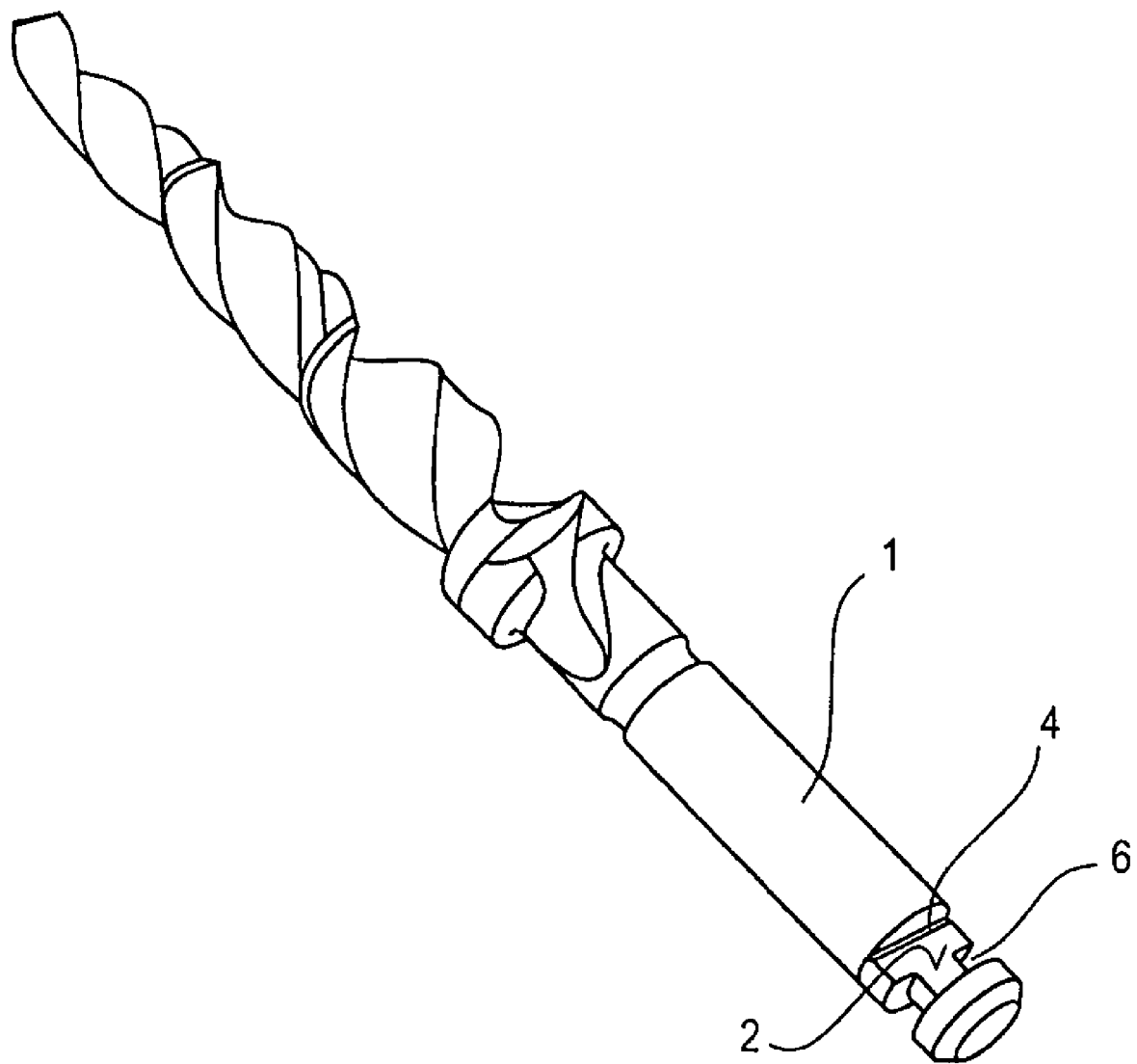
FIG. 10 is a perspective view of an instrument formed as a drill having an instrument shaft, according to the present invention.

FIG. 10 shows a perspective view of a rotating instrument formed as a spiral drill having an instrument shaft according to one of the embodiments of the present invention.

The present invention has been described in an illustrative manner. It is to be understood that the terminology, which has been used, is intended to be in the nature of words of description rather than of limitation.

Many modifications and variations of the present invention are possible in light, of the above teachings. Therefore, within the scope of the appended claims, the present invention may be practiced other than as specifically described.

What is claimed is:

1. A dental instrument shaft for a rotating instrument, said dental instrument shaft being made of a ceramic material comprising:

a cylindrical shaft end having a center axis and a first portion being cylindrical having a radial surface and a second portion being semi-cylindrical having a flat driving area arranged in parallel to the center axis, the radial surface bordering on the second portion and extending perpendicular to the flat driving area; and a groove having an arcuate cross-section extending exclusively into the radial surface of the first portion and in parallel to the driving area.

2. A dental instrument shaft as set forth in claim 1 wherein the groove is formed straight.

3. A dental instrument shaft as set forth in claim 1 including at least one outlet bevel and wherein the groove merges into the at least one outlet bevel.

4. A dental instrument shaft as set forth in claim 3 wherein the at least one outlet bevel is arranged toward the cylindrical shaft end.

5. A dental instrument shaft as set forth in claim 1 wherein the relationship between the radial cut-in-depth (b) of the groove and a shaft diameter (s) of the cylindrical shaft end ranges between 0.05/2.35 and 0.5/2.35 mm.

6. A dental instrument shaft as set forth in claim 5 wherein the relationship between a radial cut-in depth (b) of the groove and a shaft diameter (s) of the cylindrical shaft end ranges between 0.05/2.35 and 0.2/2.35 mm.

7. A dental instrument shaft as set forth in claim 1 wherein the relationship between a cut-in width (a) of the groove in an axial direction and a length (l) of the driving area in the axial direction ranges from 0.1/2.6 to 0.8/2.6 mm.

8. A dental instrument shaft as set forth in claim 1 wherein the relationship between a cut-in width (a) of the groove in an axial direction and a length (l) of the driving area in the axial direction ranges from 0.1/2.6 to 0.4/2.6 mm.

9. A dental instrument shaft as set forth in claim 1 wherein the groove has a radius (R) from a centerpoint of the groove ranging between 0.15 and 0.2 mm.

10. A dental instrument shaft as set forth in claim 1 wherein at least a portion of the groove is provided with a texture being densified by shot peening.

* * * * *